US00RE37078E

(19) United States
(12) Reissued Patent
Wierzbicki et al.

(10) Patent Number: US RE37,078 E
(45) Date of Reissued Patent: Feb. 27, 2001

(54) THIOPHENE COMPOUNDS

(75) Inventors: Michel Wierzbicki, L'Etang la Ville; Frédéric Sauveur, Argenteuil; Jacqueline Bonnet, Paris; Charles Tordjman, Boulogne, all of (FR)

(73) Assignee: Adir et Compagnie, Courbevoie (FR)

(21) Appl. No.: 09/368,343

(22) Filed: Aug. 3, 1999

Related U.S. Patent Documents

Reissue of:
(64) Patent No.: 5,705,525
Issued: Jan. 6, 1998
Appl. No.: 08/605,537
Filed: Feb. 22, 1996

(30) Foreign Application Priority Data

Feb. 23, 1995 (FR) ..... 95 02061

(51) Int. Cl.[7] ..... A61K 31/38; C07D 333/22
(52) U.S. Cl. ..... 514/438; 549/77
(58) Field of Search ..... 549/77; 514/438

(56) References Cited

U.S. PATENT DOCUMENTS 5,571,810 * 11/1996 Matsuo et al. ..... 514/231.5

* cited by examiner

*Primary Examiner*—Deborah C. Lambkin
(74) *Attorney, Agent, or Firm*—The firm of Gordon W. Hueschen

(57) ABSTRACT

The invention relates to thiophene compounds of formula:

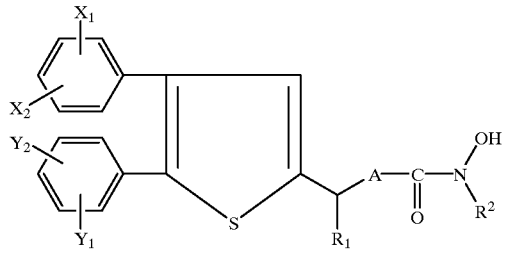

wherein:

[$X_1$, $X_2$, $Y_1$ and $Y_2$, which are identical or different, each represents hydrogen or halogen, ($C_1$–$C_5$)-alkyl or alkoxy, or trifluoromethyl,]

*$X_1$ and $Y_1$, which are identical or different, each represents $C_1$–$C_5$ alkoxy,*

*$X_2$ and $Y_2$ each represents hydrogen,*

$R_1$ represents hydrogen or ($C_1$–$C_5$)-alkyl,

A represents a straight ($C_1$–$C_5$)-hydrocarbon chain of which each carbon atom is optionally mono- or di-substituted by a ($C_1$–$C_5$)-alkyl, and $R_2$ represents hydrogen, ($C_1$–$C_6$)-alkyl, cyclohexyl or benzyl;

and their physiologically tolerable salts.

The products of the invention may be used as anti-inflammatory agents.

6 Claims, No Drawings

THIOPHENE COMPOUNDS

Matter enclosed in heavy brackets [ ] appears in the original patent but forms no part of this reissue specification; matter printed in italics indicates the additions made by reissue.

The present invention relates to new thiophene compounds.

It relates especially to compounds of formula I:

(I)

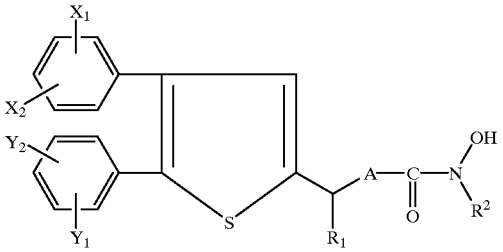

wherein

[$X_1$, $X_2$, $Y_1$ and $Y_2$, which are identical or different, each represents a hydrogen or halogen atom, an alkyl or alkoxy radical each having from 1 to 5 carbon atoms in straight or branched chain, or a trifluoromethyl radical;]

*$X_1$ and $Y_1$, which are identical or different, each represents an alkoxy radical having 1 to 5 carbon atoms in straight or branched chain,*

*$X_2$ and $Y_2$ each represents hydrogen,*

$R_1$ represents a hydrogen atom or an alkyl radical having from 1 to 5 carbon atoms in straight or branched chain;

A represents a straight hydrocarbon chain having from 1 to 5 carbon atoms each of which carbon atoms is optionally mono- or di-substituted by an alkyl radical having from 1 to 5 carbon atoms; and $R_2$ represents a hydrogen atom, an alkyl radical having from 1 to 5 carbon atoms in straight or branched chain, a cyclohexyl radical or a benzyl radical;

and their physiologically tolerable addition salts with appropriate bases.

The closest prior art to the present invention is illustrated especially by the PCT patent application 91/19708, which relates to compounds of formula:

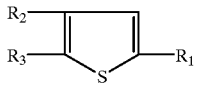

having an anti-inflammatory activity, which reference neither describes nor suggests the compounds of formula I forming the subject of the present invention; the compounds of formula I have a pharmacological and therapeutic activity of particular value in the inflammation field.

The present invention relates also to a process for the preparation of compounds of formula I which is characterised in that:

the ester of formula II:

(II)

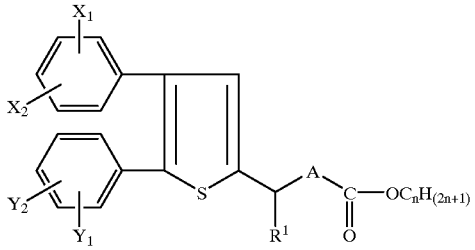

wherein $X_1$, $X_2$, $Y_1$, $Y_2$, $R_1$ and A are defined above and n represents 1 or 2 is hydrolysed to form an acid of formula III:

(III)

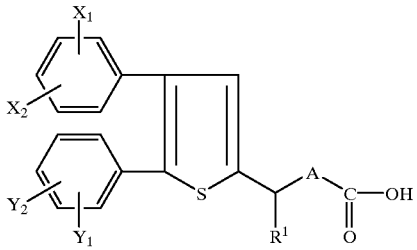

wherein $X_1$, $X_2$, $Y_1$, $Y_2$, $R_1$ and A are as defined above.

which acid is converted into a corresponding activated compound of formula IV:

(IV)

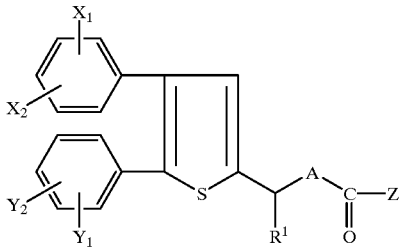

wherein $X_1$, $X_2$, $Y_1$, $Y_2$, $R_1$ and A are as defined above, and

Z represents a chlorine atom or an imidazol-1-yl radical, with which the O-silylated hydroxylamine of formula V:

(V)

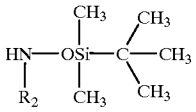

wherein $R_2$ is as defined above is reacted to obtain the compound of formula VI:

(VI)

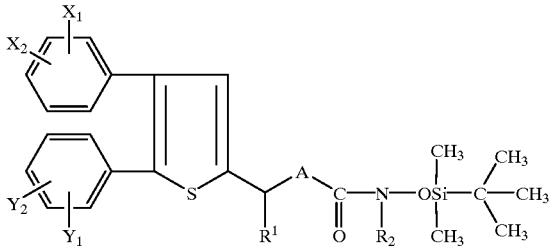

wherein $X_1$, $X_2$, $Y_1$, $Y_2$, A, $R_1$ and $R_2$ are as defined above, which is hydrolysed to obtain the corresponding compound of formula I.

The hydrolysis of the ester of formula II is expediently carried out by means of sodium hydroxide in aqueous alcohol medium.

The conversion of the acid of formula III into an activated compound of formula IV is advantageously carried out either in a chloroform medium, by means of oxalyl chloride, to obtain compounds of formula IV wherein Z represents a chlorine atom, or in a dichloromethane medium, by means of carbonyldiimidazole, to obtain the compounds of formula IV wherein Z represents an imidazol-1-yl radical.

The reaction of the compounds IV and V to yield compounds of formula VI is carried out especially expediently by operating in an appropriate solvent, such as, for example:

acetonitrile, in the presence of dimethylaminopyridine and triethylamine in the case where, in the formula of the compound IV used, Z represents a chlorine atom, and dichloromethane in the case where, in the formula of the compound IV used, Z represents an imidazol-1-yl radical.

The hydrolysis of the compound of formula VI to obtain a compound of formula I is advantageously carried out by operating in a mixture of dichloromethane and trifluoroacetic acid.

The ester of formula II, used as starting material, was prepared in accordance with the following reaction scheme:

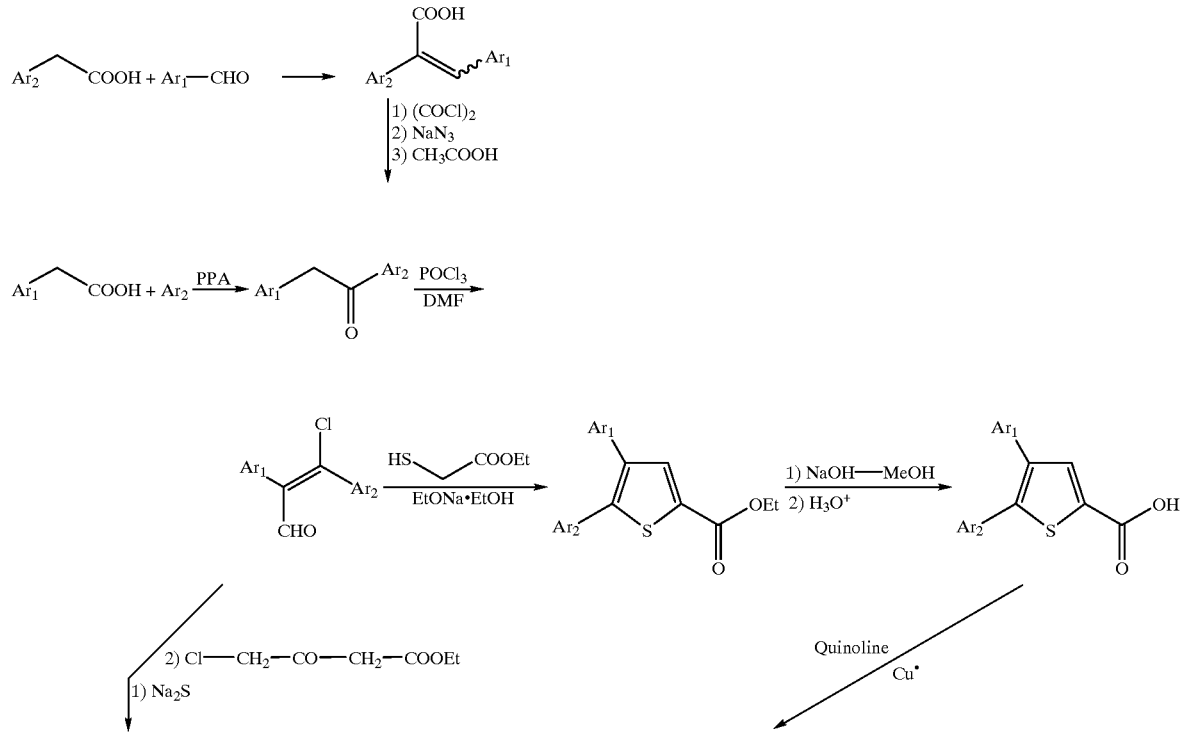

-continued

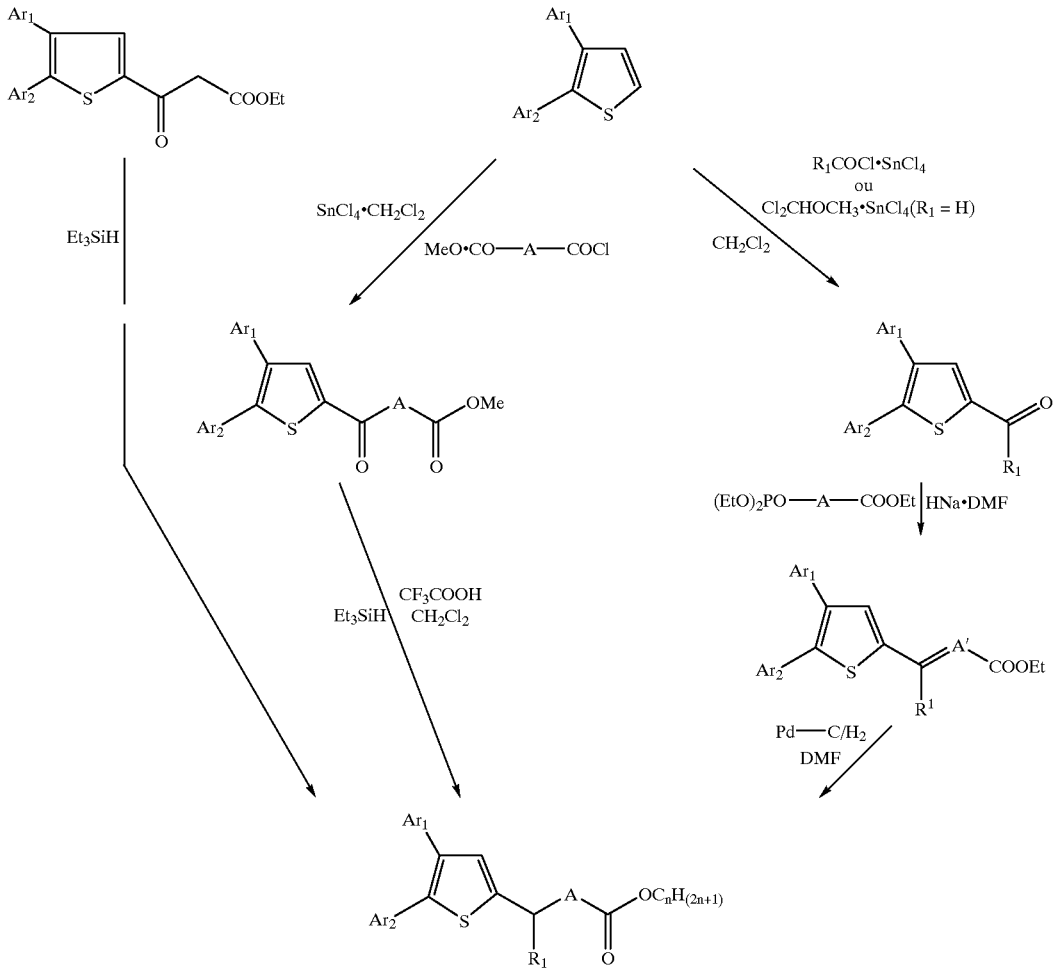

(II)

it being understood that in that scheme:

$Ar_1$ represents:

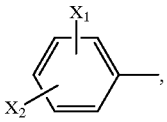

$Ar_2$ represents:

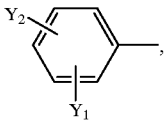

PPA=polyphosphoric acid,

DMF=dimethylformamide,

Et=—$C_2H_5$,

Me=—$CH_3$, n=1 or 2, $R_1$ and A are as defined for formula I, and

A is such that A=—HA'—

The compounds of formula I may be converted into physiologically tolerable addition salts with appropriate bases. Prepared according to conventional methods, as described in the Examples hereinafter, those salts, as such, form part of the present invention.

The compounds of the present invention have valuable pharmacological and therapeutic properties especially in the inflammation field.

During the course of inflammation, arachidonic acid, released from the phospholipids of the cellular membrane by phospholipase A2, is rapidly metabolised by two main enzymatic pathways: that of cyclooxygenase, which leads to the formation of prostaglandins, and that of lipoxygenase, which leads to the formation of leukotriene. The prostaglandins, especially $PGE_2$, play an important role in the vascular phenomena associated with inflammation as well as in inflammatory pain, while at the same time exerting a protective effect on the gastric mucosa. Two types of cyclooxygenases have been demonstrated recently: constitutive type 1 cyclooxygenase (COX1), which is found in the physiological state in various tissues of the stomach, and type 2 cyclooxygenase (COX2), which is induced during inflammatory processes. The leukotrienes—notably 5HETE and leukotrienes B4—powerful neutrophil chemoattractants, which are capable of increasing vascular permeability and have immunological properties, contribute to the progressive tissue destruction of immunoinflammatory diseases, such as rheumatoid polyarthritis; they furthermore appear to be implicated in gastric ulceration processes. The inhibition of cyclooxygenase by non-steroidal anti-inflammatories (NSAI) is responsible for their beneficial effect on the symptoms of the initial phase of inflammation, but it also has the undesirable effects that belong to that class of medicaments, especially in respect of the gastrointestinal mucosa. Those NSAIs have no effect on the progression of the tissue destruction associated with leukocyte migration.

The compounds of the present invention inhibit both the enzymatic pathway of cyclooxygenase and that of lipoxygenase. In addition, they exert a preferential inhibition of COX2 compared with COX1. That particular profile gives them powerful anti-inflammatory effects, which act in particular on the symptoms of chronicity, and an improved gastrointestinal tolerance compared with conventional NSAIs.

The compounds of the invention also prove to be powerful anti-inflammatory agents capable of inhibiting both the early vascular phase and the chronic tissue destruction phase associated with inflammation.

Their therapeutic effect will therefore be effective in rheumatological inflammation of an acute or chronic nature, such as, for example, rheumatoid polyarthritis and ankylosing spondylitis, and in inflammation of the intestinal type (Crohn's disease) or of the cutaneous type (psoriasis) in which leukotrienes are found to be implicated.

The present invention relates also to pharmaceutical compositions comprising as active ingredient a compound of formula I or a physiologically tolerable salt thereof, mixed with or in association with an appropriate pharmaceutical excipient, such as, for example, glucose, starch, talc, ethylcellulose, magnesium stearate, cocoa butter or distilled water.

The so-obtained pharmaceutical compositions are generally presented in a dosage form, which may contain from 10 to 300 mg of active ingredient; they may, for example, take the form of tablets, dragées, gelatin capsules, suppositories, injectable or drinkable solutions or ointments and, depending on the case in question, may be administered by the oral, rectal, parenteral or local route.

The dosage may vary in accordance with the age and weight of the patient, the route of administration, the nature of the disorder and associated treatments.

By way of example, the dosage by the oral route may range from 10 to 300 mg of active ingredient per day.

The following Examples illustrate the invention. Unless specified to the contrary, the melting points are determined using a Kofler hot plate.

EXAMPLE 1

3-[4,5-bis(4-methoxyphenyl)thien-2-yl]-N-hydroxy-N-methylpropionamide

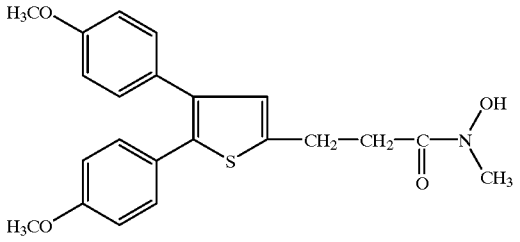

A/ Preparation of 3-[4,5-bis(4-methoxyphenyl)thien-2-yl] propionic acid 94 ml of normal sodium hydroxide solution are added to 32.6 g (0.082 mol) of ethyl 3-[4,5-bis(4-methoxyphenyl) thien-2-yl]-propionate and 94 ml of ethanol in a 1 liter three-necked flask and the whole is heated at reflux for 1 hour. After removal of the ethanol, the phase remaining is taken up in 180 ml of water and then subjected to extraction with 150 ml of ether. The aqueous layer is then acidified with 95 ml of normal hydrochloric acid and subsequently subjected to extraction twice with 300 ml of ether each time.

After drying over $MgSO_4$ and treating with animal black, then filtering and concentrating, 29 g of the expected acid are obtained in the form of a white solid which melts at 122° C. (yield: 96%).

B/ Preparation of the title compound

Into a 1 liter three-necked flask fitted with a mechanical stirring device, a thermometer and a dropping funnel, all placed in a cooling bath, there are introduced 12 g (0.0746 mol) of N-methyl-O-[(Si-dimethyl-Si-tert-butyl)silyl] hydroxylamine, 240 ml of acetonitrile, 0.9 g (0.0075 mol) of dimethylaminopyridine and 7.54 g (0.075 mol) of triethylamine freshly rectified over KOH. The reaction mixture is brought to 0° C. in a brine bath.

In the meantime, 3-[4,5-bis(4-methoxyphenyl)thien-2-yl] propionyl chloride is prepared by reacting 20.98 g of oxalyl chloride with 25 g (0.078 mol) of the acid prepared in Step A dissolved in chloroform.

After the removal of excess oxalyl chloride by distillation in vacuo, the acid chloride so obtained is dissolved in 50 ml of $CH_3CN$ and the said solution is added, in the course of 20 minutes, to the reaction mixture containing the N-methyl-O-[(Si-dimethyl-Si-tert-butyl)silyl]hydroxylamine, while maintaining the temperature at 0° C. After a few minutes' stirring, the temperature is brought to 20° C. and then the mixture is hydrolysed with 210 ml of water and diluted with 210 ml of ethyl acetate. The organic phase is decanted off and the aqueous phase is extracted twice with 100 ml of ethyl acetate each time. The combined organic phases are washed with 70 ml of a saturated NaCl solution, dried over $MgSO_4$, treated with animal black, filtered and concentrated. The crude oil obtained (35.9 g, yield: 100%) is used without being purified.

In a 1 liter, three-necked flask, fitted with a magnetic stirring device, a thermometer and a dropping funnel, all placed in a cooling bath, a solution of 35.9 g (0.0678 mol) of the product obtained above in 280 ml of dichloromethane is introduced, in the course of one hour, into a mixture of 300 ml of dichloromethane and 68.2 ml of trifluoroacetic acid, while maintaining the temperature at 0° C.

The temperature is then brought to 20° C. and the mixture is hydrolysed with 300 ml of water. The organic phase is decanted off and washed with 200 ml of 10% hydrogen carbonate and 140 ml of water. After drying over $MgSO_4$, treating with animal black, filtering and concentrating, the phase obtained is chromatographed on silica using a mixture of dichloromethane and ethyl acetate (90/10) as eluant. The useful fractions are combined and concentrated and the residue obtained is crystallised in ether, suctioned off and dried to yield 20.9 g of the title product in the form of a white crystallised solid which melts at 96° C. (yield: 78%).

The product so obtained, treated with $CaCl_2$ and NaOH in a water-methanol medium yields the corresponding calcium salt.

The same method, using $ZnCl_2$ instead of $CaCl_2$, allows the corresponding zinc salt to be obtained.

EXAMPLES 2 TO 29

By proceeding as described in Example 1, the compounds forming the subject of the Examples listed in the following Table were prepared:

Compounds of formula I: (I)

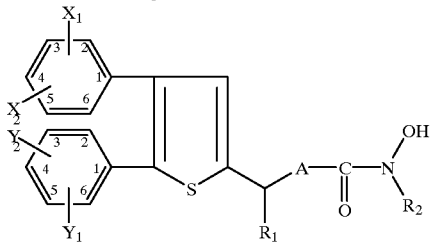

| Example n° | $X_1$ | $X_2$ | $Y_1$ | $Y_2$ | $R_1$ | A | $R_2$ | Physicochemical characteristics m.p. or IR frequency (ν, $cm^{-1}$) |
|---|---|---|---|---|---|---|---|---|
| 2 | (4)-F | H | (4)-$OCH_3$ | H | H | —$CH_2$— | —$CH_3$ | m.p.: 100° C. |
| 3 | (4)-$OCH_3$ | H | (4)-$OCH_3$ | H | H | 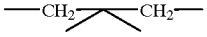 | H | amorphous powder νCO: 1642 |
| 4 | (4)-$OCH_3$ | H | (4)-$OCH_3$ | H | H | 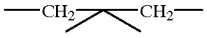 | —$CH_3$ | amorphous powder νOH: 3178 νCO:1608 |
| 5 | (4)-F | H | (4)-$OCH_3$ | H | H | 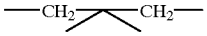 | —$CH_3$ | amorphous powder νOH: 3180 νCO:1608 |
| 6 | (4)-$OCH_3$ | H | (4)-$OCH_3$ | H | H | —$H_2C$—$CH_2$— | —$CH_3$ | m.p.: 120° C. |
| 7 | (4)-$OCH_3$ | H | (4)-$OCH_3$ | H | —$CH_3$ | —$CH_2$— | —$CH_3$ | amorphous powder νOH: 3500–3600 νCO: 1607 |
| 8 | (4)-$OCH_3$ | H | (4)-$OCH_3$ | H | H | —$CH_2$— | 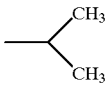 | m.p.: 130° C. |
| 9 | (4)-$CH_3$ | H | (4)-$OCH_3$ | H | H | —$CH_2$— | —$CH_3$ | m.p.: 86° C. |
| 10 | (4)-$CF_3$ | H | (4)-$OCH_3$ | H | H | —$CH_2$— | —$CH_3$ | m.p.: 120° C. |
| 11 | (4)-Cl | H | (4)-$OCH_3$ | H | H | —$CH_2$— | —$CH_3$ | m.p.: 101° C. |
| 12 | (4)-$CH_3$ | H | (4)-$OCH_3$ | H | H | 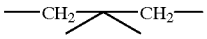 | —$CH_3$ | amorphous powder νOH: 3171 νCO: 1606 |
| 13 | (4)-$CF_3$ | H | (4)-$OCH_3$ | H | H | 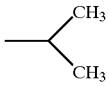 | —$CH_3$ | m.p.: 100° C. |
| 14 | (4)-$OCH_3$ | H | (4)-$OCH_3$ | H | H | —$CH_2$—$CH_2$— | 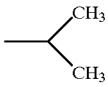 | m.p.: 136° C. |
| 15 | (4)-$OCH_3$ | H | (4)-Cl | H | H | —$CH_2$—$CH_2$— | —$CH_3$ | m.p.: 70° C. |
| 16 | (4)-$CH_3$ | H | (4)-$OCH_3$ | H | H | —$CH_2$—$CH_2$— | —$CH_3$ | $Ca^{++}$ salt m.p.: >100° C. |
| 17 | (4)-$OCH_3$ | H | (4)-Cl | H | H | —$CH_2$— | —$CH_3$ | m.p.: 100° C. |
| 18 | (4)-$OCH_3$ | H | (4)-$OCH_3$ | H | H | —$CH_2$— | 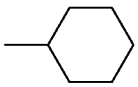 | m.p.: 140° C. |
| 19 | (4)-$OCH_3$ | H | (4)-$OCH_3$ | H | H | —$CH_2$— | 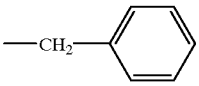 | m.p.: 104° C. |
| 20 | (4)-Cl | H | (2)-$OCH_3$ | (4)-$OCH_3$ | H | —$CH_2$— | —$CH_3$ | m.p.: 60° C. |
| 21 | (4)-Cl | H | (4)-$OCH_3$ | H | H | —$CH_2$—$CH_2$— | —$CH_3$ | m.p.: 95° C. |

-continued

Compounds of formula I: (I)

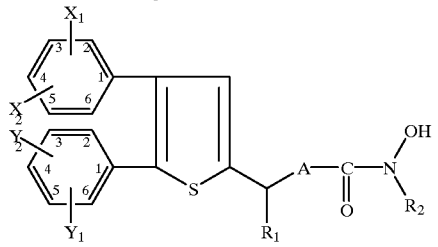

| Example n° | $X_1$ | $X_2$ | $Y_1$ | $Y_2$ | $R_1$ | A | $R_2$ | Physicochemical characteristics m.p. or IR frequency (ν, $cm^{-1}$) |
|---|---|---|---|---|---|---|---|---|
| 22 | (4)-$OCH_3$ | H | (4)-$OCH_3$ | H | H | —$CH_2$— | —$CH_2$—$CH_3$ | m.p.: 95° C. |
| 23 | (4)-$CH_3$ | H | (4)-$CH_3$ | H | H | —$CH_2$— | —$CH_3$ | $Ca^{++}$ salt m.p.: >230° C. (decomp.) νCO: 1603 characteristic band: 983 |
| 24 | (4)-$OCH_3$ | H | (4)-$OCH_3$ | H | H | —$(CH_2)_3$— | —$CH_3$ | amorphous powder νCO: 1608 |
| 25 | (4)-$OCH_3$ | H | (4)-$OCH_3$ | H | H | —$(CH_2)_4$— | —$CH_3$ | amorphous powder νCO: 1608 |
| 26 | (4)-$OCH_3$ | H | (4)-$OCH_3$ | H | H | —$(CH_2)_5$— | —$CH_3$ | amorphous powder νCO: 1609 |
| 27 | (4)-$CH_3$ | H | (4)-$OCH_3$ | H | H | —$(CH_2)_3$— | —$CH_3$ | amorphous powder νCO: 1607 |
| 28 | (4)-$OCH_3$ | H | (4)-$CH_3$ | H | H | —$(CH_2)_3$— | —$CH_3$ | amorphous powder νCO: 1607 |
| 29 | (4)-$CH_3$ | H | (4)-$OCH_3$ | H | H | —$(CH_2)_4$— | —$CH_3$ | amorphous powder νCO: 1606 |

Synthesis of the Starting Materials of Formula II

The esters of formula II used as starting material were synthesised as indicated in one or other of the methods described below. It is recommended to use:

the first method to synthesis the esters of formula II wherein A represents —$CH_2$—, and the second method in the other cases.

First Method

This method was used to prepare esters II used as starting materials in the synthesis of the compounds forming the subject of Examples 1, 2, 7 to 11, 17 to 20, 22 and 23.

It is exemplified in detail by the preparation of ethyl 3-[4,5-bis(4-methoxyphenyl)thien-2-yl) propionate, the starting material used for the synthesis of the compound forming the subject of Example 1.

1) Preparation of the compound of formula:

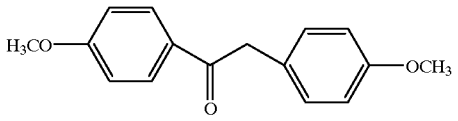

50 g of polyphosphoric acid, 20 g (0.12 mol) of 2-(4-methoxyphenyl)acetic acid and 15.2 g of anisole are poured into a 250 ml, three-necked flask that has been fitted with a mechanical stirring device and a thermometer and immersed in an oil bath. The reaction mixture is heated to 120° C. with stirring and maintained at that temperature for 45 minutes. The mixture, which turns bright red, is then briskly poured into one liter of 1N HCl. The whole is stirred vigorously for 1 hour 30 minutes. The yellow precipitate formed is filtered, washed abundantly with water and carefully suctioned off. The solid collected is dissolved in 600 ml of dichloromethane. The organic phase is washed with 200 ml of water, 100 ml of an aqueous 10% sodium hydrogen carbonate solution and finally 100 ml of water.

The organic phase is dried over magnesium sulphate, rendered colourless with animal black, filtered, concentrated and chromatographed on silica using $CH_2Cl_2$ as eluant. The useful fractions are combined and concentrated. The solid obtained is taken up in petroleum ether, filtered, suctioned off and dried in vacuo. 19.8 g of the expected product are obtained in the form of a white solid, m.p.: 158° C. Yield: 64.5%.

The following compounds were prepared by proceeding in the same manner:

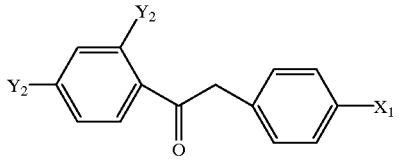

| $X_1$ | $Y_1$ | $Y_2$ | M.p. ° C. |
|---|---|---|---|
| —F | —$OCH_3$ | H | 105 |
| —$CH_3$ | —$OCH_3$ | H | 92 |
| —$CF_3$ | —$OCH_3$ | H | 150 |
| —Cl | —$OCH_3$ | H | 135 |
| —Cl | —$OCH_3$ | —$OCH_3$ | 69 |

N.B.: A variant of the above method was used for the preparation of the compound of formula:

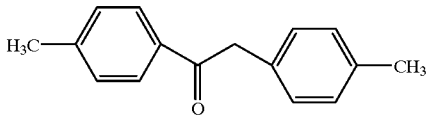

60 g of para-tolylacetic acid and 200 ml of acetic anhydride are introduced into a 1 liter, three-necked flask. 48 g of para-tolualdehyde and then, dropwise, 100 ml of triethylamine, are added to the suspension. The whole is heated under gentle reflux for 12 hours, then the acetic anhydride is distilled off. The mixture is taken up in 1 liter of ethyl acetate, then 1100 ml of N HCl are slowly added. Decanting is carried out and the organic phase is washed with 100 ml of N HCl then 100 ml of 0.1N HCl. The organic phase is concentrated by distilling off 90% of the ethyl acetate. The organic phase is filtered and the precipitate is washed with a small amount of ice-cold ethyl acetate and then with petroleum ether. In that manner 45 g of the acid of formula:

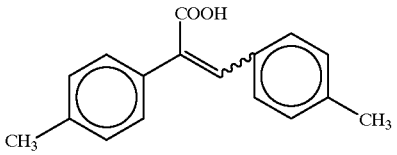

are obtained. The acid is dissolved in 1 liter of chloroform, 68 g of oxalyl chloride are added thereto, and the whole is heated at reflux until the evolution of gas has ceased. The solvent and the volatile substances are then distilled off. The acid chloride so obtained is dissolved in 200 ml of acetone and then the solution is slowly added to a mixture of 37.4 g of sodium hydrogen carbonate and 12.7 g of sodium azide in 200 ml of water and 200 ml of acetone. The mixture is stirred at room temperature for a further hour and then the acetone is distilled off under reduced pressure. Extraction is carried out with toluene, with removal of the mineral residue formed, and the organic phase is washed with water, dried over magnesium sulphate and then concentrated to dryness. In that manner 51 g of an unstable brown oil are obtained. 230 ml of acetic acid and then 125 ml of water are subsequently poured onto the oil, and the whole is heated at reflux for 1 hour and then cooled, and the resulting precipitate is filtered and washed with water and then with cold ethanol. In that manner 35.6 g of the compound of formula:

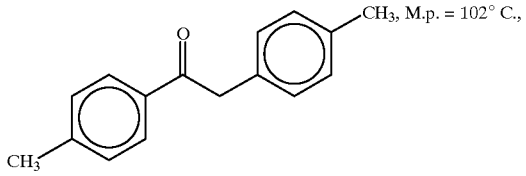

are obtained, which shall be used to prepare the ester II, the starting material for the synthesis of the compound forming the subject of Example 23.

Prepared in the same manner was the compound of formula:

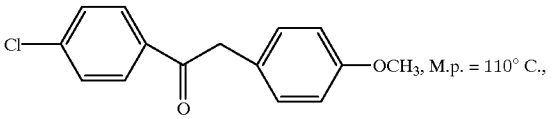

which shall be used to prepare the ester II, the starting material for the synthesis of the compounds forming the subject of Examples 15 and 17.

2) Preparation of the compound of formula:

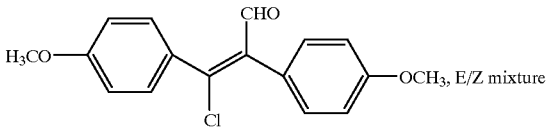

172 ml of anhydrous dimethylformamide are introduced into a 2 liter, three-necked flask, fitted with a mechanical stirring device, a thermometer and a dropping funnel, and placed in a cooling bath. The mixture is brought to 0° C. using a brine bath and, in the course of thirty minutes, 74.7 g (0.049 mol) of $POCl_3$ are added thereto. After stirring for twenty minutes, 100 g (0.39 mol) of deoxyanisoin dissolved in 700 ml of anhydrous dimethylformamide are added thereto, with stirring, in the course of 1 hour at a temperature of from 0° to 5° C. A yellow precipitate rapidly appears. The temperature of the reaction mixture is brought to 80° C. and maintained there for 6 hours. The residue is then poured into 750 ml of an aqueous 25% sodium acetate solution. The precipitate formed is filtered, washed with water, and malaxated in 1 liter of boiling ethanol. After cooling the suspension, filtering, suctioning off and drying the product, 104 g of the expected product are obtained in the form of a white solid which melts at 158° C. (yield: 88%).

The following compounds, in the form of E/Z mixtures, were prepared by proceeding in the same manner:

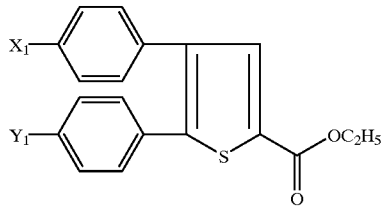

| $X_1$ | $Y_1$ | $Y_2$ | M.p. ° C. |
|---|---|---|---|
| —F | —$OCH_3$ | H | 128 |
| —$CH_3$ | —$OCH_3$ | H | 126 |
| —$CF_3$ | —$OCH_3$ | H | 125 |
| —Cl | —$OCH_3$ | H | 126 |
| —Cl | —$OCH_3$ | —$OCH_3$ | 128 |
| —$OCH_3$ | —Cl | H | 113 |
| —$CH_3$ | —$CH_3$ | H | 145 |

3) Preparation of the compound of formula:

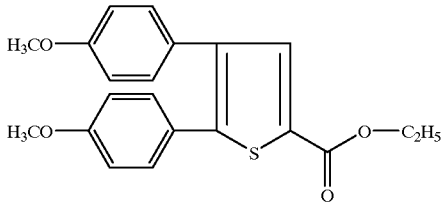

Into a 2 liter, three-necked flask that has been fitted with a mechanical stirring device, a thermometer and a dropping funnel and immersed in an oil bath there are poured 450 ml of anhydrous ethanol to which 6.7 g (0.29 mol) of sodium are added little by little. The mixture is then heated at reflux until dissolution is complete. After cooling, 28 g (0.231 mol) of ethyl 2-mercaptoacetate dissolved in 100 ml of anhydrous ethanol are rapidly added. The colourless solution obtained is cooled to 0° C. on brine. The chloroformyl derivative prepared in section 2) above is then added in portions in the course of 30 minutes. The mixture is stirred for 4 hours, then brought to room temperature. A fine precipitate appears. After distilling off the ethanol, the residue is taken up in 650 ml of anhydrous ether and frozen for 48 hours. The sodium chloride is filtered off and the ethereal solution is concentrated. The residue, reprecipitated from 100 ml of isopropanol, yields 72 g of the expected product in the form of a yellow solid which melts at 75° C. (yield: 84%).

The following compounds were prepared by proceeding in the same manner:

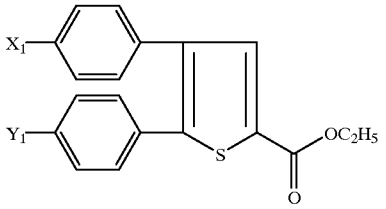

| $X_1$ | $Y_1$ | M.p. ° C. |
|---|---|---|
| —F | —$OCH_3$ | 120 |
| —$CH_3$ | —$OCH_3$ | 115 |
| —$CF_3$ | —$OCH_3$ | 88 |
| —Cl | —$OCH_3$ | 95 |
| —$OCH_3$ | —Cl | 90 |
| —$CH_3$ | —$CH_3$ | 76 |

4) Preparation of the compound of formula:

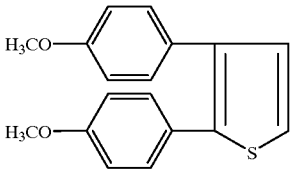

In a 1 liter single-necked flask fitted with a condenser and a mechanical stirring device, 71.7 g (0.194 mol) of the above-prepared ester are suspended in 197 ml of ethanol and 197 ml of 1N sodium hydroxide solution. The mixture is heated to reflux and stirred for 1 hour. The solid rapidly dissolves. The ethanol is distilled off under reduced pressure. The residue is taken up in 200 ml of water. The aqueous phase, washed 3 times with 100 ml of ether each time, is acidified with 50 ml of 4N HCl. The yellow precipitate obtained is filtered, washed with water then with a few ml of ice-cold ethanol, a few ml of ether and finally with petroleum ether. After drying in air, 51 g of a white solid, which is [4,5-bis(4-methoxyphenyl)thien-2-yl]carboxylic acid, are obtained, m.p.: 215° C. (yield: 77%).

30 g of that solid are suspended in 180 ml of quinoline to which 1 g of copper powder has been added. The mixture is heated on an oil bath to 180° C. and is maintained at that temperature until the evolution of gas has ceased, that is to say 45 minutes. After cooling, the residue is poured into a mixture of 520 g of water and 325 ml of concentrated HCl. The aqueous phase is extracted 3 times with 650 ml of ether each time. The ethereal phase is washed with 200 ml of water, 200 ml of aqueous 10% sodium hydrogen carbonate and then with 200 ml of water.

After treatment with $MgSO_4$ and animal black, the organic phase is concentrated and the residue is crystallised from 100 ml of petroleum ether, filtered, suctioned off and dried in air. 24.7 g of the expected product are obtained in the form of a white solid which melts at 113°–114° C. (yield: 95%).

The following compounds were prepared by proceeding in the same manner:

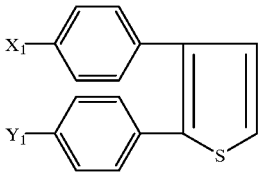

| $X_1$ | $Y_1$ | M.p. ° C. |
|---|---|---|
| —F | —$OCH_3$ | 80 |
| —$CH_3$ | —$OCH_3$ | 60 |
| —$CF_3$ | —$OCH_3$ | 88 |
| —Cl | —$OCH_3$ | 96 |
| —$OCH_3$ | —Cl | 110 |
| —$CH_3$ | —$CH_3$ | 85 |

starting, respectively, from the following intermediate acids:

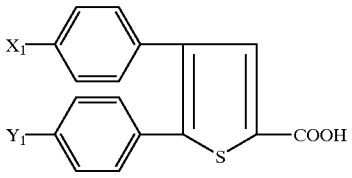

| $X_1$ | $Y_1$ | M.p. ° C. |
|---|---|---|
| —F | —$OCH_3$ | 185 |
| —$CH_3$ | —$OCH_3$ | 234 |
| —$CF_3$ | —$OCH_3$ | 206 |
| —Cl | —$OCH_3$ | 212 |
| —$OCH_3$ | —Cl | 218 |
| —$CH_3$ | —$CH_3$ | 264 |

5) Preparation of the compound of formula:

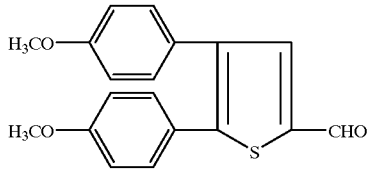

29.6 g (0.0998 mol) of 2,3-bis(4-methoxyphenyl) thiophene [prepared as in section 4)] dissolved in 450 ml of anhydrous dichloromethane are introduced into a 2 liter, three-necked flask that has been fitted with a mechanical stirring device, a thermometer and a dropping funnel and placed under a stream of nitrogen. The mixture is brought to −50° C. and 13.3 g (0.115 mol) of dichloromethyl ether are added in one batch and 35.3 g (0.135 mol) of $SnCl_4$ are then added in the course of 20 minutes at −50° C. (a brown colour appears). The temperature is returned to 20° C. and the mixture is hydrolysed with a water-ice (150 g)/concentrated HCl (25 ml) mixture. The organic phase is decanted off and the aqueous phase is extracted twice with 50 ml of dichloromethane each time. The combined organic phases are washed with 60 ml of 1N HCl, 60 ml of water, 60 ml of sodium hydrogen carbonate and finally 60 ml of water, and then treated with $MgSO_4$ and animal black before being concentrated. The residue is crystallised from 80 ml of ether; the precipitate is filtered, suctioned-off and dried in air. 28.5 g of the expected product are thus obtained in the form of a white solid which melts at 122° C. (yield: 88%).

The following compounds were prepared by proceeding in the same manner:

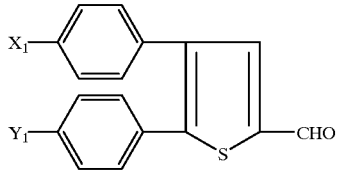

| $X_1$ | $Y_1$ | M.p. ° C. |
|---|---|---|
| —F | —$OCH_3$ | amorphous |
| —$CH_3$ | —$OCH_3$ | 112 |
| —$CF_3$ | —$OCH_3$ | 130 |
| —Cl | —$OCH_3$ | 128 |
| —$OCH_3$ | —Cl | 105 |
| —$CH_3$ | —$CH_3$ | 85 |

6) Preparation of the compound of formula:

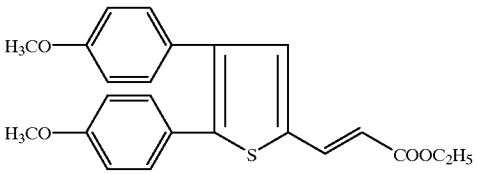

In a 1 liter three-necked flask fitted with a mechanical stirring device, a thermometer and a dropping funnel, 3.85 g (0.0963 mol) of sodium hydride are suspended in 63 ml of anhydrous dimethylformamide, then 21.6 g (0.0963 mol) of triethyl phosphonoacetate dissolved in 182 ml of anhydrous dimethylformamide are added in the course of 40 minutes. The reaction is exothermic. After 30 minutes' stirring, the temperature is brought to 20° C. and 28.5 g (0.0878 mol) of aldehyde dissolved in 103 ml of anhydrous dimethylformamide are added in the course of 20 minutes. Stirring of the mixture is continued for 10 hours (orange solution). The dimethylformamide is distilled off under reduced pressure. The residue is taken up in 120 ml of water and then extracted 3 times with 300 ml of ether each time. The organic phase is dried over $MgSO_4$, treated with animal black, filtered and concentrated. 33.6 g of the expected product are obtained in the form of a white solid which melts at 88°–90° C. (yield: 97%).

The following compounds were prepared by proceeding in the same manner:

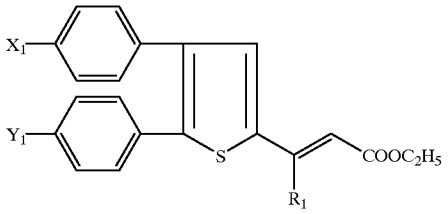

| $R_1$ | $X_1$ | $Y_1$ | M.p. ° C. |
|---|---|---|---|
| H | —F | —$OCH_3$ | 118 |
| H | —$CH_3$ | —$OCH_3$ | 87 |
| H | —$CF_3$ | —$OCH_3$ | 123 |
| H | —Cl | —$OCH_3$ | amorphous |
| (*) $CH_3$ | —$OCH_3$ | —$OCH_3$ | amorphous |
| H | —$OCH_3$ | —Cl | crude oil used without purification |
| H | —$CH_3$ | —$CH_3$ | crude oil used without purification |

(*) NB: This compound was prepared from 2,3-bis(4-methoxyphenyl)thiophene substituted in the 5 position by the radical —$COCH_3$, itself prepared in accordance with the method described in section 5) above.

Preparation of compounds of formula:

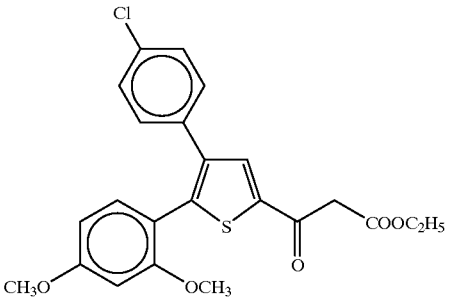

11.9 g of sodium sulphide monohydrate and 50 ml of dimethylformamide are introduced into a 500 ml three-necked flask. 5 drops of triethylamine are added and then 15.2 g of 2-(4-chlorophenyl)-2-(_-chloro-2,4-dimethoxybenzylidene)acetaldehyde dissolved in 100 ml of dimethylformamide are added. The whole is stirred for 1 hour at room temperature and then cooled to −10° C. 7.4 g of ethyl 4-chloroacetyl acetate dissolved in 13 ml of dimethylformamide are added. The whole is stirred at −10° C. for 1 hour then at room temperature for 24 hours. The whole is poured into 1 liter of saturated NaCl solution. The gummy solid formed is filtered, taken up in dichloromethane and chromatographed on silica using dichloromethane as eluant. In that manner 8.5 g of ~95% pure product are obtained.

7) Preparation of ethyl 3-[4,5-bis(4-methoxyphenyl) thien-2-yl]propionate:

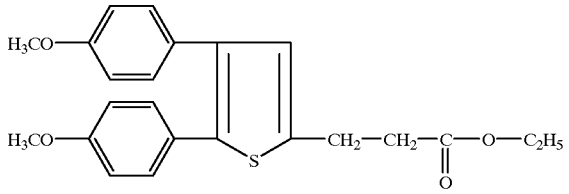

(starting material used in Example 1):

33.6 g (0.085 mol) of the ethylene compound prepared in section 6) are dissolved in 900 ml of anhydrous dimethylformamide and charged into a low-pressure hydrogenator. 9 g of 10% palladium-on-carbon are added thereto. After several purges, the hydrogen is introduced under $5.5\times10^5$ Pa and the reaction mixture is stirred vigorously. When hydrogen is no longer absorbed, the reaction is continued for 15 minutes at 50° C. After cooling, the solution is filtered, the dimethylformamide is removed in vacuo, and the residue is dissolved in 20 ml of an ether/petroleum ether mixture (50/50). After filtration over paper, the solvents are distilled off. 32.6 g of the expected product are obtained in the form of a pale yellow oil. (Yield: 96.7%).

The following compounds were prepared by proceeding in the same manner:

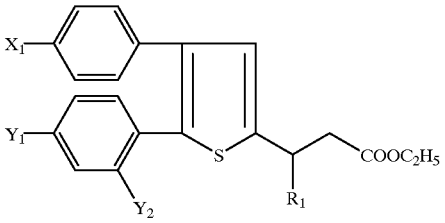

| $R_1$ | $X_1$ | $Y_1$ | $Y_2$ | I.R. νCO ($cm^{-1}$) |
|---|---|---|---|---|
| H | —F | —$OCH_3$ | H | 1733 |
| H | —$CH_3$ | —$OCH_3$ | H | 1734 |
| H | —$CF_3$ | —$OCH_3$ | H | 1735 |
| H | —Cl | —$OCH_3$ | H | 1734 |
| $CH_3$ | —$OCH_3$ | —$OCH_3$ | H | 1733 |
| H | —$OCH_3$ | —Cl | H | 1733 |
| H | —$CH_3$ | —$CH_3$ | H | 1735 |
| H | —Cl | —$OCH_3$ | —$OCH_3$ | 1734 |

Second Method

This method was used to prepared the esters II used as starting materials in the synthesis of the compounds forming the subject of Examples 3 to 6, 12 to 16 and 21. By way of example, it is described in detail below for the preparation of methyl 5-[4,5-bis(4-methoxyphenyl)thien-2-yl)-3,3-dimethylpentanoate, the starting material used for the synthesis of the compound forming the subject of Example 3.

1) Preparation of the compound of formula:

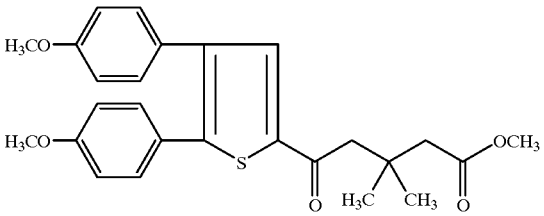

3 g (0.0101 mol) of 2,3-bis(4-methoxyphenyl)thiophene [prepared as described in the first method, section 4)], dissolved in 32 ml of anhydrous dichloromethane, are introduced into a 250 ml three-necked flask fitted with a magnetic stirring device, a thermometer and a dropping funnel and placed in a cooling bath. The mixture is cooled to 0° C. on brine, then methyl 3,3-dimethylglutarate chloride prepared from 1.75 g (0.01 mol) of methyl 3,3-dimethylglutarate and 2 ml of thionyl chloride are added thereto. 39 g (0.015 mol) of $SnCl_4$ are then added in the course of 10 minutes (a red colour appears). After 30 minutes' stirring, the residue is hydrolysed with a water-ice (20 g)/concentrated HCl (2 ml) mixture. The aqueous phase is extracted 3 times with 30 ml of dichloromethane each time. The organic phase is washed with 20 ml of 1N HCl, 20 ml of aqueous 10% sodium hydrogen carbonate and finally with 20 ml of water. After treatment with $MgSO_4$ and animal black, filtration and concentration, 4.7 g of the expected product are obtained in the form of a colourless oil (yield: 100%).

The following compounds were prepared by proceeding in the same manner:

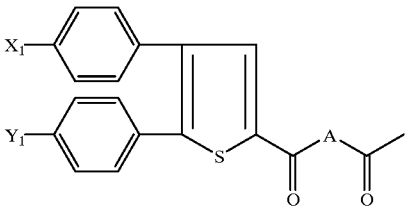

| $X_1$ | $Y_1$ | A | M.p. (° C.) | νCO ester ($cm^{-1}$) | νCO ketone ($cm^{-1}$) |
|---|---|---|---|---|---|
| —F | —$OCH_3$ | —$H_2C$—$CH_2$— | 66 | 1734 | 1651 |
| —$CH_3$ | —$OCH_3$ | —$H_2C$—$CH_2$— | oil | 1735 | 1650 |
| —$CF_3$ | —$OCH_3$ | —$H_2C$—$CH_2$— | oil | 1734 | |
| —$OCH_3$ | —$OCH_3$ | —$H_2C$—$CH_2$— | 96 | 1741 | 1667 |
| —$CH_3$ | —$OCH_3$ | —$H_2C$—$CH_2$— | oil | 1734 | 1658 |
| —Cl | —$OCH_3$ | —$H_2C$—$CH_2$— | 106 | 1741 | 1662 |
| —$OCH_3$ | —Cl | —$H_2C$—$CH_2$— | 112 | 1743 | 1665 |
| —$OCH_3$ | —$OCH_3$ | —$(CH_2)_3$— | oil | 1734 | 1650 |
| —$OCH_3$ | —$OCH_3$ | —$(CH_2)_4$— | oil | 1734 | 1650 |
| —$OCH_3$ | —$OCH_3$ | —$(CH_2)_5$— | oil | 1735 | 1651 |
| —$CH_3$ | —$OCH_3$ | —$(CH_2)_3$— | oil | 1733 | 1650 |
| —$OCH_3$ | —$CH_3$ | —$(CH_2)_3$— | oil | 1733 | 1651 |
| —$CH_3$ | —$OCH_3$ | —$(CH_2)_4$— | oil | 1732 | 1651 |

2) Preparation of methyl 5-[4,5-bis(4-methoxyphenyl) thien-2-yl]-3,3-dimethylpentanoate:

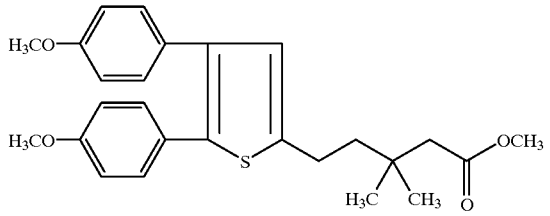

(used as starting material for the synthesis of the compounds forming the subject of Examples 3 and 4).

5.94 g (0.0131 mol) of the compound prepared as described above in section 1) and 5.98 g (0.052 mol) of trifluoroacetic acid are added to 10 ml of anhydrous dichloromethane in a 100 ml three-necked flask fitted with a magnetic stirring device, a condenser and a thermometer. 3.04 g (0.0262 mol) of triethylsilane are then added in the course of 10 minutes. The mixture is heated at reflux for 8 hours and 3.04 g of triethylsilane are added again. After 10 hours' additional reflux, the residue is concentrated, taken up in 20 ml of dichloromethane and washed with 20 ml of a saturated aqueous sodium hydrogen carbonate solution and then with 20 ml of water. After treatment with $MgSO_4$ and animal black, filtration and chromatography on a silica column using dichloromethane as eluant, concentration of the useful fractions yields 17 g of the expected product in the form of a colourless oil (yield: 67%).

The following compounds were prepared by proceeding in the same manner:

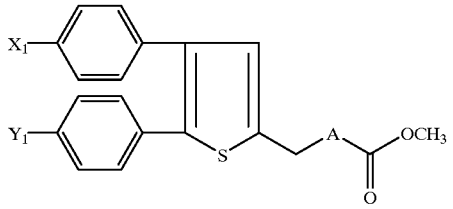

| $X_1$ | $Y_1$ | A | M.p. ° C. |
|---|---|---|---|
| —F | —$OCH_3$ | —$H_2C$—$CH_2$— | amorphous product |
| —$CH_3$ | —$OCH_3$ | —$H_2C$—$CH_2$— | oil |
| —$CF_3$ | —$OCH_3$ | —$H_2C$—$CH_2$— | oil |
| —$OCH_3$ | —$OCH_3$ | —$H_2C$—$CH_2$— | 78 |
| —$CH_3$ | —$OCH_3$ | —$H_2C$—$CH_2$— | 140 |
| —Cl | —$OCH_3$ | —$H_2C$—$CH_2$— | oil |
| —$OCH_3$ | —Cl | —$H_2C$—$CH_2$— | oil |
| —$OCH_3$ | —$OCH_3$ | —$(CH_2)_3$— | oil |
| —$OCH_3$ | —$OCH_3$ | —$(CH_2)_4$— | oil |
| —$OCH_3$ | —$OCH_3$ | —$(CH_2)_5$— | oil |
| —$CH_3$ | —$OCH_3$ | —$(CH_2)_3$— | oil |
| —$OCH_3$ | —$CH_3$ | —$(CH_2)_3$— | oil |
| —$CH_3$ | —$OCH_3$ | —$(CH_2)_4$— | oil |

EXAMPLE 30

Pharmacological Study

1) The effect of the compounds of the invention on the biosynthesis of mediators of the cyclooxygenase pathway on the one hand and of the lipoxygenase pathway on the other hand were demonstrated in vitro on rat polymorphonucleocytes stimulated by the ionophore A23187 in accordance with the protocol described by C. Tordjman et al. ("High-performance liquid chromatographic quantitation of cyclooxygenase and lipoxygenase metabolites of arachidonic acid from rat polymorphonuclear leucocytes" Journal of Chromatography, 532, 1990, 135–143).

The results obtained are assembled in the following Table:

| | $IC_{50}$ ($\mu$M) | |
|---|---|---|
| COMPOUNDS | cyclooxygenase pathway ($PGE_2$) | lipoxygenase pathway (LTB4) |
| Example 1 | 0.05 | 0.03 |
| Example 2 | 0.38 | 0.08 |
| Example 3 | 2.50 | 1.00 |
| Example 4 | 0.75 | 0.38 |
| Example 5 | 2.50 | 0.25 |
| Example 6 | 0.38 | 0.05 |
| Example 16 | 0.05 | 0.05 |
| Example 22 | 0.08 | 0.05 |

2) The in vivo activity of the compounds of the invention was studied in an acute inflammatory pain test in the mouse—Siegmund test ("Screening of analgesics, including aspirin-type compounds, based upon the antagonism of chemically induced "writhing" in mice" J. Pharm. Exp. Ther. 119, 1957, 184). For example, after oral administration of the compounds, a 50% inhibition of the reactions of the animal was caused by a dose of 1 mg/kg in the case of the compound of Example 1, of 2.5 mg/kg in the case of the compound of Example 6 and of 5 mg/kg in the case of the compound of Example 2.

3) The activity on chronic inflammation was evaluated in a polyarthritis auto-immune model in the rat using Freund's adjuvant in accordance with the protocol described by J. Bonnet et al. ("Bone morphometric changes in adjuvant-induced polyarthritic osteopenia in rats; evidence for an early bone formation defect" J. Bone Miner. Res. 8, 1993, 659–668). By way of example, the compound of Example 1, at an oral dose of 5 mg/kg/day, inhibits by 30% the diffusion of arthritis on the 14th day of the pathology.

4) Conclusion: the above results show that the compounds tested are powerful anti-inflammatory agents capable of inhibiting both the early vascular phase and the chronic tissue destruction phase associated with inflammation. It will therefore be possible, as a result of that fact, for the compounds to be used in the treatment of rheumatological inflammation of an acute or chronic nature (rheumatoid polyarthritis, ankylosing spondylitis) and inflammation of the intestinal type (Crohn's disease) or of the cutaneous type (psoriasis) in which leukotrienes are found to be implicated.

We claim:

1. A thiophene compound selected from those of formula I:

(I)

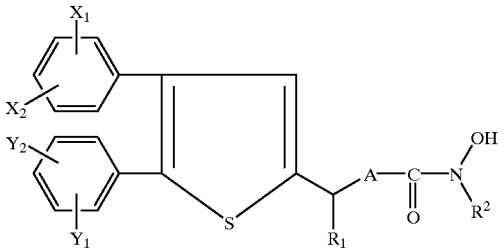

wherein:

[$X_1$, $X_2$, $Y_1$ and $Y_2$ $X_1$ *and* $Y_1$, which are identical or different, each represents ($C_1$–$C_5$) alkoxy each in straight or branched chain,

*$X_2$ and $Y_2$ each represents hydrogen,*

$R_1$ represents hydrogen;

A represents a straight ($C_1$–$C_2$) hydrocarbon chain, and $R_2$ represents ($C_1$–$C_5$) alkyl in straight or branched chain;

and physiologically tolerable addition salts thereof with appropriate bases.

2. A compound of claim 1 selected from the group consisting of 3-[4,5-bis(4-methoxyphenyl) thien-2-yl]-N-hydroxy-N-methylpropionamide and a calcium salt thereof.

3. A compound of claim 1 which is 4-[4,5-bis(4-methoxyphenyl) thien-2-yl]-N-hydroxy-N-methylbutanamide.

4. A compound of claim 1 which is 3-[4,5-bis(4-methoxyphenyl) thien-2-yl]-N-ethyl-N-hydroxypropionamide.

5. A method for treating a living animal body afflicted with a rheumatological inflammation or inflammation of the intestinal or cutaneous type in which leukotrienes are implicated, comprising the step of administering to the living animal body an amount of a compound of claim 1 which is effective for alleviation of said condition.

6. A pharmaceutical composition useful in the treatment of rheumatological inflammation comprising as active ingredient a compound according to claim 1, in combination with one or more pharmaceutical excipients.

* * * * *